United States Patent [19]

Takai et al.

[11] Patent Number: 4,966,981
[45] Date of Patent: Oct. 30, 1990

[54] PROCESS FOR PREPARING EPOXY GROUP-CONTAINING SILANES

[75] Inventors: Haruko Takai, Chiba; Taiji Sakiyama, Urayasu; Kimishige Matsuzaki, Yokohama; Toshio Nozaki, Kamakura; Yoshiharu Okumura, Shinjuku; Chihiro Imai, Yokohama, all of Japan

[73] Assignee: Toa Nenryo Kogyo Kabushiki Kaisha, Tokyo, Japan

[21] Appl. No.: 490,540

[22] Filed: Mar. 5, 1990

Related U.S. Application Data

[63] Continuation of Ser. No. 184,612, Apr. 21, 1988, abandoned.

[30] Foreign Application Priority Data

Apr. 22, 1987 [JP] Japan ................................. 62-98883

[51] Int. Cl.$^5$ ............................................ C07D 303/22
[52] U.S. Cl. ..................................... 549/215; 549/214
[58] Field of Search ........................................ 549/215

[56] References Cited

U.S. PATENT DOCUMENTS

| | | | |
|---|---|---|---|
| 3,787,452 | 1/1974 | Leumann et al. | 549/215 |
| 4,028,384 | 6/1977 | Vahlensieck et al. | 549/215 |
| 4,083,856 | 4/1978 | Mendicino | 549/215 |

FOREIGN PATENT DOCUMENTS

| | | | |
|---|---|---|---|
| 3023622 | 1/1981 | Fed. Rep. of Germany | 549/215 |
| 50-24947 | 8/1975 | Japan | 549/215 |

Primary Examiner—Glennon H. Hollrah
Assistant Examiner—Susan P. Treanor
Attorney, Agent, or Firm—Wenderoth, Lind & Ponack

[57] ABSTRACT

In a process for the preparation of epoxy group-containing alkoxy silanes by hydrosililation of a terminally unsaturated epoxy compound with a hydro-alkoxy silane using a platinum catalyst, the improvement comprising carrying out the hydrosililation in the presence of an alcohol. By this process formation of the internally sililated isomer can be suppressed and the desired terminally sililated poduct can be produced at an approximately 100% selectivity.

4 Claims, No Drawings

PROCESS FOR PREPARING EPOXY GROUP-CONTAINING SILANES

This application is a continuation of now abandoned application, Ser. No. 07/184,612 filed on Apr. 21, 1988.

FIELD OF THE INVENTION

The present invention relates to a process for preparing epoxy group-containing silanes. More particularly it relates to a improvement in a process for the preparation of epoxy group-containing alkoxy silanes by hydrosililation of a terminally unsaturated epoxy compound with a hydro-alkoxy silane using a platinum catalyst.

BACKGROUND OF THE INVENTION

Silane coupling agents are compounds having in the molecule an organic functional group and a hydrolizable group reactive with inorganic materials. Since the silane coupling agents are, due to their functional groups. capable of chemically bonding an organic polymer with an inorganic material, such as silica, thereby to remarkably increase the mechanical strength of the organic polymer, a demand of them is increasing as an indispensable material in the development of ultrafashionable composite materials.

Among others, silane coupling agents having an epoxy group in the molecule find wide applications in the fields of electronic materials. Because of very severe requirements for heat resistance and insulating properties in electronic materials, highly pure silane coupling agents having an epoxy group in the molecule are desired in the art.

It is already known in the art that epoxy group-containing alkoxy silanes can be prepared by hydrosililation of a terminally unsaturated epoxy compound with a hydro-alkoxy silane using a platinum catalyst. For example, Japanese Patent Publication No.49-25651 discloses a process wherein 3-glycidoxypropylalkoxysilane is prepared by hydrosililation of allylglycidylether with a hydro-alkoxy silane using as a catalyst a complex of platinum dichloride with an unsaturated ketone such as mesityl oxide. Japanese Patent Publication No.50-24947 discloses a process wherein the reaction of allylglycidylether with a hydro-alkoxy silane is carried out in the presence of a complex of platinum with a beta-diketone such as acetylacetone as a catalyst.

However, there has been a problem in that when a terminally unsaturated epoxy compound is hydrosililated with a hydro alkoxy silane in the presence of a platinum catalyst, in addition to a desired terminally sililated product, an undesired Internally sililated isomer is inevitably produced. For example, when allylglycidylether is hydrosililated with trimethoxysilane using a platinum catalyst, the reaction proceeds as illustrated below, whereby 2-glycidoxyisopropyltrimethoxysilane (undesired isomer, β-isomer) is produced in addition to 3-glycidoxypropyltrimethoxysilane (desired product, γ-isomer).

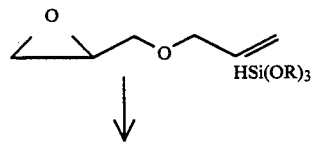

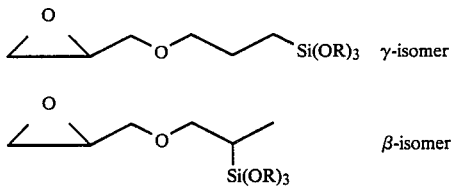

It is generally very difficult to separate the desired product from the undesired isomer by distillation, since the difference in the boiling point between them is very small. Accordingly, it is desired to provide a process for the preparation of epoxy group-containing alkoxy silanes by which formation of the internally sililated isomer can be suppressed and the desired terminally sililated product can be produced at the highest possible selectivity.

OBJECT OF THE INVENTION

The invention is to solve the above-discussed problem associated with the prior art, and an object of the invention is to provide an improvement in a process for the preparation of epoxy group-containing alkoxy silanes by hydrosililation of a terminally unsaturated epoxy compound with a hydro-alkoxy silane using a platinum catalyst by which formation of the internally sililated isomer can be suppressed and the desired terminally sililated product can be produced at the highest possible selectivity.

SUMMARY OF THE INVENTION

It has now been found that if the hydrosililation of a terminally unsaturated epoxy compound with a hydro-alkoxy silane using a platinum catalyst is carried out in the presence of an alcohol, formation of the internally sililated isomer can be suppressed and the desired terminally sililated product can be produced at the highest possible selectivity. Thus, the invention provides an improvement in a process for the preparation of epoxy group-containing alkoxy silanes by hydrosililation of a terminally unsaturated epoxy compound with a hydro-alkoxy silane using a platinum catalyst, which improvement comprises carrying out the hydrosililation in the presence of an alcohol.

DETAILED DESCRIPTION OF THE INVENTION

The invention will now be described in detail.

Products of the process according to the invention are epoxy group-containing alkoxy silanes. They are useful as silane coupling agents. Among them, particularly useful compounds as epoxy group-containing silane coupling agents are those of the general formula (I)

ti RCH$_2$CH$_2$SI(OR$^1$)$_n$R$^2{}_{3-n}$ (I)

wherein R is an epoxy-containing organic group free from active hydrogen. R$^1$ and R$^2$ each represents alkyl having from 1 to 3 carbon atoms and n is an integer from 1 to 3. Particularly preferred products are compounds of the general formula(I) wherein R is glycidoxymethyl, 3,4-epoxycyclohexyl, oxiranyl, oxiranylphenyl, 3,4-epoxybutyl. oxiranylmethyl, oxiranylethyl and 2-methylglyeidoxymethyl; R$^1$ and R$^2$ are selected from the group consisting of methyl and ethyl; and n is 2 or 3.

Any terminally unsaturated epoxy compounds that have heretofore been used for the preparation of epoxy group containing silanes by hydrosililation thereof can be used herein. Those suitable for the preparation of epoxy group-containing alkoxy silanes of the general formula (I) may be represented by the general formula (II)

$$RCH_2=CH_2 \quad (II)$$

wherein R is as defined above. Examples of preferred terminally unsaturated epoxy compounds of the general formula (II) include, for example, allylglycidylether, 4 vinylcyclohexene-1-oxide, 3-butadieneoxide, divinylbenzeneoxide, 1,5-hexadieneoxide, 1,4-pentadieneoxide, 3-methyl-1,3-butadiene-1-oxide and allyl(alphamethylglycidyl)ether.

Any hydro-alkoxy silanes having from 1 to 3 alkoxy groups that have heretofore been used for the hydrosililation of terminally unsaturated epoxy compounds can be used herein. Hydro-alkoxy silanes suitable for the preparation of epoxy group-containing alkoxy silanes of the general formula (I) may be represented by the general formula (III)

$$HSi(OR^1)_nR^2{}_{3-n} \quad (III)$$

wherein $R^1$, $R^2$ and n are as defined above. Of these, preferred hydro-alkoxy silanes which can be used herein are those of the general formula(III), wherein $R^1$ and $R^2$ are selected from the group consisting of methyl and ethyl; and n is 2 or 3. Examples of preferred hydro-alkoxy silanes include. For example, trimethoxysilane. triethoxysilane, methyldimethoxysilane and ethyldiethoxysilane.

Any platinum catalysts that have heretofore been used for the hydrosililation of terminally unsaturated epoxy compounds with hydrosilanes can be used. Preferred platinum catalysts include, for example, hexachloroplatinic acid; complexes of a platinum chloride with an unsaturated ketone such as dichloro(mesityl oxide)platinum(II) and dichloro(methylvinylketone)-platinum(II), complexes of a platinum chloride with a beta diketone such as dichloroplatinum(II)acetylacetonate, complexes of a platinum chloride with an olefin such as dichloro(1,5-cyclooctadiene)platinum(II), complexes of a platinum chloride with an amine such as dichlorodiammineplatinum(II) and complexes of a platinum chloride with a phosphine such as dichlorobis(triphenylphosphine)platinum(II).

The amount of the platinum catalyst used may range from $10^{-7}$ to $10^{-3}$ mole, preferably from $10^{-6}$ to $10^{-4}$ mole, per mole of the hydro-alkoxy silane.

Alcohols which can be used herein include, for example, methanol, ethanol, n-propanol, and isopropanol.

For the purpose of the invention it is desirable to use the alcohol in an amount of more than 0.1 mole, preferably from about 0.2 to about 10 moles, more preferably from about 0.5 to about 3.0 moles, per mole of the hydro-alkoxy silanes. With substantially less than about 0.2 mole of the alcohol per mole of the hydro alkoxy silane, the formation of the internally sililated isomer is not satisfactorily suppressed. On the other hand, it is advantageous to avoid use of an excessive amount of the alcohol, or otherwise a side reaction such as noted below may tend to occur.

$$HSi(OR^1)_3 + R^1OH \rightarrow Si(OR^1)_4 + H_2$$

The alcohol is preferably admixed with the hydroalkoxy silane reactant and the admixture is added to a mixture of the unsaturated epoxy compound reactant and the catalyst under stirring, followed by continuation of the reaction.

Other conditions which can be used herein are the same as have heretofore been used in the preparation of epoxy group containing silanes by hydrosililation of a terminally unsaturated epoxy compound with a hydro-alkoxy silane.

In carrying out the present reaction, the unsaturated epoxy compound may be used in a range from about 0.5 to about 2.0 moles, preferably from about 0.7 to 1.3 moles, per mole of the hydro-alkoxy silane. The reaction temperature is normally from ambient temperature to about 100° C., preferably from about 40 to 70° C. The reaction time may normally be from about 0.5 to about 3.0 hours. While the reaction is normally carried out under atmospheric pressure, it may be carried out under elevated pressures.

EFFECT OF THE INVENTION

By the process according to the invention in which a terminally unsaturated epoxy compound is hydrosililated with a hydro-alkoxy silane using a platinum catalyst in the presence of an alcohol, formation of the undesired internally sililated product can be effectively suppressed, and the desired terminally sililated product can be prepared at a selectivity as high as approximately 100%.

While the invention is illustrated by the following examples, the invention is not limited thereto.

EXAMPLE 1

A four neck flask equipped with a dropping funnel, a reflux condenser, a stirrer and a thermometer, was charged with 13.7 grams (0 12 mole) of allyglycidylether and 12μl of a 0.1M solution of hexachloroplatinic acid ($H_2PtCl_6.6H_2O$) in isopropyl alcohol ($1.2 \times 10^{-6}$ mole as platinum). and heated to a temperature of 50° C. under stirring. To the mixture maintained at that temperature under stirring, a mixture of 12.2 grams (0.1mole) of trimethoxysilane and 6.4 grams (0.2 mole) of methanol was dropwise added over a period of 2 hours. The reaction mixture was further maintained at 50° C. under stirring for 1 hour.

At the end of the period, it was revealed by gas chromatography analysis that the desired 3-glycidoxypropyltrimethoxysilane had been obtained at a yield of 90.0% (on a trimethoxysilane basis) and that a yield ratio by weight of the desired product to the internally sililated product was 99.5:0.5

By simple distillation of the reaction mixture, 3-glycidoxypropyltrimethoxysilane of a purity of 99.7% was obtained.

EXAMPLE 2

Example 1 was repeated except that methanol was used in an amount of 1.6 grams (0.05 mole) instead of the 6.4 grams (0.2 mole)

Gas chromatography analysis revealed that the desired 3-glycidoxypropyltrimethoxysilane had been obtained at a yield of 91.1% (on a trimethoxysilane basis) and that a yield ratio by weight of the desired product to the internally sililated product was 99.4:0.6.

By simple distillation of the reaction mixture. 3-glycidoxypropyltrimethoxysilane of a purity of 99.6% was obtained.

EXAMPLE 3

A four-neck flask equipped with a dropping funnel, a reflux condenser, a stirrer and a thermometer, was charged with 13.7 grams (0.12 mole) of allylglycidylether and 12μl of a 0.1M solution of hexachloroplatinic acid ($H_2 PtCl_6$, $6H_2O$) in isopropyl alcohol ($1.2 \times 10^{-6}$ mole as platinum). and heated to a temperature of 80° C. under stirring. To the mixture maintained at that temperature under stirring, a mixture of 16.4 grams (0.1 mole) of triethoxysilane and 4.6 grams (0.1 mole) of ethanol was dropwise added over a period of 2 hours. The reaction mixture was further maintained at 80° C. under stirring for 1 hour.

At the end of the period, it was revealed by gas chromatography analysis that the desired 3-glycidoxypropyltriethoxysilane had been obtained at a yield of 88.2% (on a triethoxysilane basis) and that a yield ratio by weight of the desired product to the internally sililated product was 9.6:0.4.

By simple distillation of the reaction mixture, 3-glycidoxypropyltriethoxysilane of a purity of 99.8% was obtained.

EXAMPLE 4

A four-neck flask equipped with a dropping funnel, a reflux condenser, a stirrer and a thermometer, was charged with 13.6 grams (0.11 mole) of 4-vinylcyclohexene-1-oxide and 12μl of a 0.1M solution of hexachloroplatinic acid ($H_2 PtCl_6.6H_2O$) in isopropyl alcohol ($1.2 \times 10^{-6}$ mole as platinum). and heated to a temperature of 50° C. under stirring. To the mixture maintained at that temperature under stirring, a mixture of 12.2 grams (0.1 mole) of trimethoxysilane and 6.4 grams (0.2 mole) of methanol was dropwise added over a period of 2 hours. The reaction mixture was further maintained at 50° C. under stirring for 1 hour.

At the end of the period, it was revealed by gas chromatography analysis that the desired 4-(2-trimethoxysilylethyl)cyclohexene-1-oxide had been obtained at a yield of 99.2% (on a trimethoxysilane basis) and that a yield ratio by weight of the desired product to the internally sililated product was 99.7:0.3

By simple distillation of the reaction mixture, 4-(2-trimethoxysilylethyl)cyclohexene-1-oxide of a purity of 99.9% was obtained.

EXAMPLE 5

A four-neck flask equipped with a dropping funnel. a reflux condenser, a stirrer and a thermometer, was charged with 7.7 grams (0.11 mole) of butadiene monooxide and 12μl of a 0.1M solution of hexachloroplatinic acid ($H_2 PtCl_6.6H_2O$) in isopropyl alcohol ($1.2 \times 10^{-6}$ mole as platinum), and heated to a temperature of 50° C. under stirring. To the mixture maintained at that temperature under stirring, a mixture of 12.2 grams (0.1 mole) of trimethoxysilane and 6.4 grams (0.2 mole) of methanol was dropwise added over a period of 2 hours. The reaction mixture was further maintained at 50° C. under stirring for 1 hour.

At the end of the period, it was revealed by gas chromatography analysis that the desired 2-trimethoxysilylethyl oxide had been obtained at a yield of 99.5% (on a trimethoxysilane basis) and that a yield ratio by weight of the desired product to the internally sililated product was 99.6:0.4.

By simple distillation of the reaction mixture, 2-trimethoxysilylethylethylene oxide of a purity of 99.8% was obtained.

EXAMPLE 6

A four-neck flask equipped with a dropping funnel, a reflux condenser, a stirrer and a thermometer, was charged with 13.7 grams (0.12 mole) of allylglycidylether and 12μl of a 0.1M solution of a complex of mesityl oxide-platinum dichloride in acetone ($1.2 \times 10^{-6}$ mole as platinum), and heated to a temperature of 80° C. under stirring. To the mixture maintained at that temperature under stirring, a mixture of 12.2 grams (0.1 mole) of trimethoxysilane and 6.4 grams (0.2 mole) of methanol was dropwise added over a period of 2 hours. The reaction mixture was further maintained at 80° C. under stirring for 1 hour.

At the end of the period, it was revealed by gas chromatography analysis that the desired 3-glycidoxypropyltrimethoxy silane had been obtained at a yield of 90.1%. (on a trimethoxysilane basis) and that a yield ratio by weight of the desired product to the internally sililated product was 99.7:0.3.

By simple distillation of the reaction mixture. 3-glycidoxypropyltrimethoxysilane of a purity of 99.9% was obtained.

EXAMPLE 7

A four-neck flask equipped with a dropping funnel, a condenser for collecting a distillate, a stirrer and a thermometer, was charged with 50 grams of finely divided metallic silicon, 1.25 grams of cuprous chloride and 10 ml of dibenzyltoluene, and heated to a temperature of 220° C. under stirring. To the mixture maintained at that temperature under stirring, 300 grams of methanol was dropwise added over a period of 6 hours. The distillate so obtained gas 255 grams in weight, and contained by weight 14.6% of methanol, 64.8% of trimethoxysilane and 30.5% of tetramethoxysilane.

Example 1 was repeated except that the mixture of methanol and trimethoxysilane used in Example 1 was replaced with 22.3 grams of the above distillate (containing 0.1mole of trimethoxysilane and 0.1 mole of methanol).

Gas chromatography analysis revealed that the desired 3-glycidoxypropyltrimethoxysilane had been obtained at a yield of 89.9% (on a trimethoxysilane basis) and that a yield ratio by weight of the desired product to the internally sililated product was 99.3:0.7.

By simple distillation of the reaction mixture, 3-glycidoxypropyltrimethoxysilane of a purity of 99.5% was obtained.

COMPARATIVE EXAMPLE 1

Example 1 was repeated except that the methanol was not used.

Gas chromatography analysis revealed that the desired 3-glycidoxypropyltrimethoxysilane had been obtained at a yield of 90.2% (on a trimethoxysilane basis) and that a yield ratio by weight of the desired product to the internally sililated product was 97.9:2.1.

By simple distillation of the reaction mixture, 3-glycidoxypropyltrimethoxysilane of a purity of 98.0% was obtained.

COMPARATIVE EXAMPLE 2

Example 1 was repeated except that the methanol used in Example 1 was replaced with 6.1 grams of benzene(50% by weight on the basis of the trimethoxysilane used).

Gas chromatography analysis revealed that the desired 3-glycidoxypropyltrimethoxysilane had been obtained at a yield of 90.8% (on a trimethoxysilanebasis) and that a yield ratio by weight of the desired product to the internally sililated product was 98.0:2.0.

By simple distillation of the reaction mixture, 3-glycidoxypropyltrimethoxysilane of a purity of 98.1% was obtained.

COMPARATIVE EXAMPLE 3

Example 3 Was repeated except that the ethanol was not used.

Gas chromatography analysis revealed that the desired 3-glycidoxypropyltriethoxysilane had been obtained at a yield of 89.1% (on a triethoxysilanebasis) and that a yield ratio by weight of the desired product to the internally sililated product was 98.2:1.8.

By simple distillation of the reaction mixture, 3-glycidoxypropyltrimethoxysilane of a purity of 98.3% was obtained.

What is claimed is:

1. In a process for the preparation of epoxy group-containing alkoxy silanes by hydrosililation of a terminally unsaturated epoxy compound with a hydro-alkoxy silane using a platinum catalyst, the improvement which comprises carrying out the hydrosilylation in the presence of an alcohol in an amount of from 0.2 to 10 moles, per mole of the hydro-alkoxy silane, said alcohol being selected from the group consisting of methanol, ethanol, n-propanol and isopropanol.

2. The process in accordance with claim 1 wherein the terminally unsaturated epoxy compound is allylglycidylether, 4-vinylcyclohexene-1-oxide, 1,3butadiene oxide, divinylbenzene oxide, 1,5-nexadiene oxide, i,4-pentadiene oxide, 3-methyl-1,3-butadiene oxide or allyl(alpha-methylglycidyl)ether.

3. The process in accordance with claim 1 wherein the hydro-alkoxy silane is trimethoxysilane, or ethoxysilane, methyldimethoxysilane or ethyldiethoxysilane.

4. The process in accordance with claim 1 wherein the platinum catalyst is hexachloroplatinic acid, a complex of a platinum chloride with an unsaturated ketone, a complex of a platinum chloride with a beta-diketone, a complex of a platinum chloride with an olefin or a complex of a platinum chloride with an amine.

* * * * *

UNITED STATES PATENT AND TRADEMARK OFFICE
CERTIFICATE OF CORRECTION

PATENT NO. : 4,966,981

DATED : October 30, 1990

INVENTOR(S) : Haruko TAKAI et al.

It is certified that error appears in the above-identified patent and that said Letters Patent is hereby corrected as shown below:

Column 1, line 22, change "groups." to --groups,--;

Column 1, line 54, change "undesired Internally" to --undesired internally--;

Column 2, line 28, change "catalyst by which" to --catalyst, by which--;

Column 2, line 57, change "ti $RCH_2CH_2SI(OR^1)_n R^2_{3-n}$" to --$RCH_2CH_2Si(OR^1)_n R^2_{3-n}$--;

Column 2, line 60, change "hydrogen." to --hydrogen,--;

Column 2, line 65, change "3,4-epoxybutyl." to --3,4-epoxybutyl,--;

Column 2, line 66, change "2-methylglyeidoxymethyl;" to --2-methylglycidoxymethyl;--;

Column 3, line 14, change "3-butadieneoxide," to --1,3-butadieneoxide,--;

Column 3, line 28, change "Of these." to --Of these,--;

Column 3, line 33, change "include. For example, trimethoxysilane." to --include, for example, trimethoxysilane,--;

Column 3, line 68, change "$Hsi(OR^1)_3 + R^1OH \rightarrow Si(OR^1)_4 + H_2$" to --$HSi(OR^1)_3 + R^1OH \rightarrow Si(OR^1)_4 + H_2$--;

Column 4, line 39, change "(0 12 mole)" to --(0.12 mole)--;

Column 4, line 42, change "($1.2 \times 10^{-6}$ mole as platinum)." to --($1.2 \times 10^{-6}$ mole as platinum),--;

Column 5, line 1, change "reaction mixture." to --reaction mixture,--;

UNITED STATES PATENT AND TRADEMARK OFFICE
CERTIFICATE OF CORRECTION

PATENT NO. : 4,966,981

DATED : October 30, 1990

INVENTOR(S) : Haruko TAKAI et al.

It is certified that error appears in the above-identified patent and that said Letters Patent is hereby corrected as shown below:

Column 5, line 11, change "($1.2 \times 10^{-6}$ mole as platinum)." to --($1.2 \times 10^{-6}$ mole as platinum),--;

Column 5, line 23, change "9.6:0.4." to --99.6:0.4.--;

Column 5, line 35, change "$1.2 \times 10^{-6}$ mole as platinum)." to --($1.2 \times 10^{-6}$ mole as platinum),--;

Column 5, line 53, change "dropping funnel." to --dropping funnel,--;

Column 5, line 66-67, change "2-trimethoxysilylethyl oxide" to --2-trimethoxysilyethylethylene oxide--;

Column 6, line 24, change "90.1%." to --90.1%--;

Column 6, line 27, change "reaction mixture." to --reaction mixture,--;

Column 6, line 40, change "so obtained gas" to --so obtained was--;

Column 6, line 41, change "64.8% of trimethoxysilane" to --54.8% of trimethoxysilane--;

Column 7, line 17, change "Example 3 Was" to --Example 3 was--;

Column 8, line 6, change "hydrosilylation" to --hydrosililation--;

Column 8, line 14, change "1,5-nexadiene" to --1,5-hexadiene--;

Column 8, line 15, change "i,4-pentadiene" to --1,4-pentadiene--;

UNITED STATES PATENT AND TRADEMARK OFFICE
CERTIFICATE OF CORRECTION

PATENT NO. : 4,966,981
DATED : October 30, 1990
INVENTOR(S) : Haruko Takai et al It is certified that error appears in the above-indentified patent and that said Letters Patent is hereby corrected as shown below:

Column 8, lines 18-19 change "or ethoxysilane" to read --triethoxysilane--.

Signed and Sealed this

Twelfth Day of October, 1993

Attest:

BRUCE LEHMAN

Attesting Officer

Commissioner of Patents and Trademarks